United States Patent [19]

Khanna et al.

[11] Patent Number: 4,489,157

[45] Date of Patent: Dec. 18, 1984

[54] CHLORAMPHENICOL DERIVATIVES

[75] Inventors: Pyare L. Khanna, San Jose; Evan S. Snyder, Mountain View; Prithipal Singh, Sunnyvale, all of Calif.

[73] Assignee: Syva Company, Palo Alto, Calif.

[21] Appl. No.: 306,569

[22] Filed: Sep. 28, 1981

[51] Int. Cl.$^3$ .............. G01N 33/54; C12Q 1/32; C12N 9/96; C07G 7/00

[52] U.S. Cl. .............................. 435/7; 435/26; 435/188; 435/810; 260/121; 260/112 B; 260/112 R

[58] Field of Search .............. 260/112 B, 112 R, 121; 435/7, 177, 188, 805, 810, 26; 564/213

[56] References Cited

U.S. PATENT DOCUMENTS 2,483,885 10/1949 Crooks et al. .................. 564/213
3,817,837 6/1974 Rubenstein et al. .............. 435/7

OTHER PUBLICATIONS

Hamburger et al., Chloramphenicol-Specific Antibody II Reactivity to Analogs of Chloramphenicol Immunology, 1969, vol. 17, pp. 587-591.

*Primary Examiner*—Sam Rosen
*Assistant Examiner*—Shawn P. Foley
*Attorney, Agent, or Firm*—Bertram I. Rowland; Theodore J. Leitereg

[57] ABSTRACT

Chloramphenicol derivatives are provided for use in the preparing of antigen conjugates for the production of antibodies specifically for chloramphenicol. Specifically, the aryl amino group is derivatized to introduce a non-oxocarbonyl group which is used for amide formation with an antigen. The conjugate is then injected into a vertebrate for production of antisera which is isolated in conventional ways and finds particular use in competitive protein binding assays.

9 Claims, No Drawings

CHLORAMPHENICOL DERIVATIVES

BACKGROUND OF THE INVENTION

1. Field of the Invention

In performing immunoassays, it is necessary to have a receptor which specifically recognizes the compound or compounds of interest while having weak or no binding to compounds of similar structure which may be encountered in the samples of interest. In order to obtain antisera when haptens are involved, it is necessary that derivatives of the hapten be designed for conjugation to an antigen, where the resulting antisera will provide for the desired specificity. In many situations, the hapten of interest is highly functionalized, so that the synthetic procedure for the derivative must be designed to maintain the integrity of the structural features of the haptens and expose the features for producing highly specific antibodies.

2. Description of the Prior Art

U.S. Pat. No. 3,817,837 describes a homogeneous enzyme immunoassay. Hamburger and Douglass, Immunology 1969, 17(4), 599–602; Orgel and Hamburger, ibid, 1971, 20(2), 233-9; Hamburger and Douglass, ibid, 1969, 17(4), 58791 and Hamburger, Science 152 (379), 203-5 (1966) describe various antibodies to chloramphenicol.

SUMMARY OF THE INVENTION

Chloramphenicol derivatives are prepared for conjugation to poly(amino acids) to prepare antigens for the production of antibodies and to prepare enzyme conjugates, where the enzyme conjugates and antibodies are used in combination in immunoassays for the determination of chloramphenicol. Particularly, the aliphatic amino group of N-dichloroacetyl free chloramphenicol (free base) is functionalized to provide a carbonyl functionality containing linking group to react with the amino groups of poly(amino acids) to provide antigen conjugates or enzyme conjugates. The conjugated antigens are employed in conventional ways for the production of antibodies specific for chloramphenicol. The antibodies are used in conjunction with the enzyme conjugate in immunoassays.

DESCRIPTION OF THE SPECIFIC EMBODIMENTS

The subject invention is concerned with the preparation of reagents for use in diagnostic immunoassays for chloramphenicol. Specifically, the aliphatic amino group of the chloramphenicol free base is functionalized to provide for an oxo-carbonyl functionality for linking to available amino groups of the poly(amino acid). The carbonyl functionality will normally be separated from the aliphatic amino group by a chain of at least about 2 atoms and not more than about 8 atoms, preferably 2 to 4 atoms. The atoms may be carbon, nitrogen, chalcogen (oxygen and sulfur), usually carbon and oxygen, there normally being from 0 to 1 heteroatom in the chain, where the heteroatoms are bonded solely to carbon atoms, with chalcogen normally bonded to saturated carbon and heteroatoms usually separated by two carbon atoms, except for non-oxo-carbonyl derivatives. With oxo-carbonyl, a single bond will usually be formed by reductive amination with available amino groups of the poly(amino acid), while with carboxy groups, peptide bonds will normally be formed. The carboxy derivative can be activated in a variety of ways to form peptide bonds.

For the preparation of antibodies, the chloramphenicol derivative will be conjugated to an, antigenic poly(amino acid), which may then be injected into vertebrates, particularly domestic animals, for production of antibodies. After a repeated number of injections based on a predetermined schedule, the antibodies may be harvested from the serum and may be used as obtained or further purified so as to concentrate the antibodies of interest.

For the most part, compositions of this invention will have the following formula:

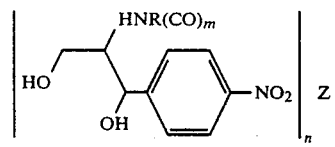

wherein:

R is an aliphatic linking group of from 2 to 12 atoms other than hydrogen, normally having from about 2 to 8 atoms in the chain, preferably 2 to 6, more preferably 3 to 5, wherein the atoms in the chain are carbon, nitrogen, and chalcogen of atomic number 8 to 16 (oxygen and sulfur), wherein the heteroatoms are bonded to other than hydrogen, and chalcogen is bonded solely to saturated carbon; of particular interest are 1-oxopolymethylenes with the oxo bonded to the nitrogen.

Z is hydrogen, hydroxyl, alkoxyl of from about 1 to 6 carbon atoms, more usually of 1 to 3 carbon atoms, an activating group capable of activating the non-oxo-carbonyl for forming peptide bonds in an aqueous medium with a poly(amino acid) e.g. p-nitrophenyl ester or N-oxy succinimide ester or Y, wherein Y is a poly(amino acid) residue, either a polypeptide or protein having 1 or more subunits, of at least about 5000, more usually at least about 10,000 molecular weight and may be 10,000,000 or more molecular weight, usually not more than 600,000, functioning as either an antigen or enzyme;

m is 0 or 1, being 1 when Z is other than Y; and n is at least 1, being 1 when Z is other than Y and when Z is Y being 1 to the molecular weight of Y divided by 500, more usually divided by 2000, generally being from about 1 to 100 when Y acts as an antigen and is of molecular weight of from about 30,000 to 300,000 and of from about 1 to 30, more usually 2 to 20, when Y functions as an enzyme.

Preferred R groups include alkylene, alkenylene, alkyleneoxyalkylene (wherein heteroatoms are separated by at least 2 carbon atoms), N-lower alkyl (1–3 carbon atoms) alkyleneaminoalkylene (wherein the heteroatoms are separated by at least 2 carbon atoms).

The compounds of primary interest are those where Z is Y and find use as antigen or enzyme conjugates, Y being a poly(amino acid), either antigenic or an enzyme. These compounds will for the most part have the following formula:

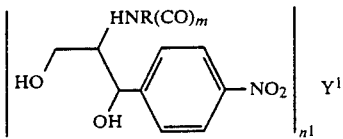

wherein R and m have been defined previously;

$Y^1$ is a poly(amino acid), functioning as an antigen or enzyme, of at least about 5000 molecular weight, more usually of at least about 10,000 molecular weight and may be up to 10,000,000 molecular weight or greater, generally not exceeding about 600,000 molecular weight, more usually not exceeding about 300,000 molecular weight;

$n^1$ is at least 1, usually greater than 1, and generally not exceeding the molecular weight of $Y^1$ divided by 500, more usually divided by 2000 and will usually be at least the molecular weight of $Y^1$ divided by 100,000, more usually the molecular weight of $Y^1$ divided 50,000, generally being from about 1 to 100, more usually from about 5 to 80, when $Y^1$ is functioning as an antigen, and from about 1 to 30, more usually 2 to 20, when $Y^1$ is functioning as an enzyme.

With intermediate molecular weight antigens, those having molecular weights in the range of about 20,000 to 600,000 the number of chloramphenicol groups which are bonded to the antigen will generally be from about 5 to 100, more usually from about 20 to 90, while with low molecular weight antigens, those from about 2000 to 10,000 molecular weight, the number will generally be from about 1 to 20, more usually 2 to 10.

As indicated previously, of particular interest are compounds where the oxo-carbonyl group (other than keto) and the non-oxo-carbonyl group are bonded to an amino group, which is part of a polypeptide or protein structure. One group of polypeptides and proteins is antigenic, so that by bonding the carbonyl derivative of chloramphenicol to the polypeptide or protein, antibodies can be formed to chloramphenicol. A narrower class of proteins, which also can be used as antigens, but will not normally be used as such, are enzymes which are employed as the detector in an immunoassay system. As antigens, inactive enzymes can be used.

Polypeptides (referred to generally in the invention as poly(amino acid)) usually encompass from about 2 to 100 amino acid units (usually less than about 12,000 molecular weight). Larger polypeptides are arbitrarily called proteins. Proteins are usually composed of from 1 to 20 polypeptide chains called subunits, which are associated by covalent or noncovalent bonds. Subunits are normally of from about 100 to 300 or higher amino acid groups (or 10,000 to 35,000 or higher molecular weight). For the purposes of this invention, poly(amino acid) is intended to include individual polypeptide units and polypeptides which are subunits of proteins, whether composed solely of polypeptide units or polypeptide units in combination with other functional groups, such as porphyrins, as in haemoglobin or cytochrome oxidase.

While the chloramphenicol analog may be bonded through the non-oxo-carbonyl group to hydroxyl or mercapto groups, which are present in the poly(amino acids), for the most part the bonding will be to amino. Therefore, the compounds are described as amides, although esters and thioesters may also be present. The aldehyde derivative will be bonded solely to amino to form alkylamine groups through reductive amination.

Amino acids present in proteins which have free amino groups for bonding to the carbonyl-modified-chloramphenicol include lysine, N-terminal amino acids, etc. The hydroxyl and mercaptan containing amino acids include serine, cysteine, tyrosine and threonine.

Various protein and polypeptide types may be employed as the antigenic material. These types include albumins, serum proteins, e.g. globulins, ocular lens proteins, lipoproteins, etc. Illustrative proteins include bovine serum albumin, keyhole limpet hemocyanin, egg albumin, bovine gamma-globulin, etc. Small neutral polypeptides which are immunogenic such as gramicidins may also be employed. Various synthetic polypeptides may be employed, such as polymers of lysine, glutamic acid, phenylalanine, tyrosine, etc., either by themselves or in combination. Of particular interest is polylysine or a combination of lysine and glutamic acid. Any synthetic polypeptide must contain a sufficient number of free amino groups as, for example, provided by lysine.

The second group of protein molecules are the detectors. These are the enzymes to which the carbonyl modified chloramphenicol may be conjugated. As indicated, the chloramphenicol conjugated enzyme is useful for immunoassays. A description of the immunoassay technique will follow.

Enzymes will normally be of molecular weights in the range of about 10,000 to 600,000, usually in the range of about 12,000 to 150,000, and more usually in the range of 12,000 to 80,000. Some enzymes will have a plurality of enzyme subunits. It is intended when speaking of enzyme molecular weights to refer to the entire enzyme. There will be on the average at least about 1 chloramphenicol per enzyme, when the labeling is not limited to a specific amino group, and rarely more than 30 chloramphenicols per enzyme, usually not more than 20 chloramphenicols per enzyme. For example, with lysozyme the average number of chloramphenicol groups would be in the range of about 2 to 5. For glucose-6-phophate dehydrogenase the average number will be in the range of 2 to 16.

Various enzymes may be used such as peptidases, esterases, amidases, phosphorylases, carbohydrases, oxidases, e.g. dehydrogenase, reductases, and the like. Of particular interest are such enzymes as lysozyme, peroxidase, α-amylase, β-galactosidase, dehydrogenases, particularly malate dehydrogenase and glucose-6-phosphate dehydrogenase, alkaline phosphatase, β-glucuronidase, cellulase and phospholipase. In accordance with the I.U.B. Classification, the enzymes of interest are: 1. Oxidoreductases, particularly Groups 1.1, and more particularly 1.1.1, and 1.11, more particularly, 1.11.1; and 3. Hydrolases, particularly 3.2, and more particularly 3.2.1.

The substituted enzymes will for the most part have the following formula:

wherein:

m and R have been defined previously;

$Y^2$ is an enzyme substituted at other than the active site, and having at least 30, preferably at least 50 percent of its original activity prior to conjugation; and $n^2$ will usually be of from 1 to 30, more usually from 2 to 20, preferably 2 to 14, more preferably 2 to 12, but generally on the average not more than about 60 percent of the total lysine groups available in the enzyme, although small enzymes such as lysozyme may have all available lysine groups conjugated.

In forming the various amide products which find use in the subject invention, the carboxylic acid will normally be activated. This can be achieved in a number of ways. Two ways of particular interest are the reaction with a carbodiimide, usually a water soluble dialiphatic or dicycloaliphatic carbodiimide in an inert polar solvent, e.g. dimethylformamide, acetonitrile or hexamethylphosphamide. The reaction is carried out by bringing the various reagents together under mild conditions and allowing sufficient time for the reaction to occur.

Another way is to use esters of the carboxy modified chloramphenicol which are operative in water for acylating amine functions. Illustrative of groups bonded to carboxy to provide activated esters which can be used in water are p-nitrophenyl and N-succinimidyl. For the aldehyde conjugation, a reductive amination is carried out in a polar, usually aqueous medium, employing sodium cyanoborohydride as the reducing agent.

The antibodies which are prepared in response to the conjugated antigens of this invention have strong specific binding to the parent drug, the conjugated antigen, the compound or derivative thereof used to conjugate to the antigen, and the chloramphenicol labeled compounds, e.g. enzyme conjugates.

As previously indicated, the subject enzyme conjugates and antibodies find use in immunoassays. The enzyme conjugates of the subject invention are particularly useful in the method described in U.S. Pat. No. 3,817,837. In performing an effective immunoassay, there are many considerations. Since the aforementioned assay is spectrophotometric, one desires that there be a substantial change in signal with changing concentration of the analyte in the range of interest of the analyte. Thus, the antigenic conjugate must provide antibodies which when employed in combination with the enzyme conjugate, results in a sensitive response to variations in the chloramphenicol concentration.

In addition, there are a number of considerations about the antigen. Normally, one immunizes a number of animals with the antigen. Initial bleeds tend to have low titer of low binding affinity, but within a relatively short time a plateau of titer and affinity is reached. A good antigen provides a high titer and a high average affinity with most or all the animals immunized. One of the significant advantages of a high affinity high titer is that one can use smaller amounts of the antisera in that the antibody of interest is a larger proportion of the total amount of gamma-globulin.

There is the further consideration of cross-reactivity. When determining a drug, one does not wish other drugs or naturally occurring compounds which may be present in the sample to affect the observed signal. Where other compounds are able to bind to various degrees to the antisera, the other compounds can have a substantial affect on the signal. This can be particularly true with metabolites, which do not have the same physiologic activity as the drug. Thus, in many situations, the antigen precursor must be designed to provide antibodies which will not significantly bind to metabolites of the analyte of interest.

EXPERIMENTAL

The following examples are offered by way of illustration and not by way of limitation.

All temperatures not otherwise indicated are centigrade. Percents and parts not otherwise indicated are by weight, except for mixtures of liquids which are by volume. Abbreviations which are employed are as follows: THF—tetrahydrofuran; tlc—thin layer chromatography; DCC—dicyclohexyl carbodiimide; NHS—N-hydroxy succinimide; HOAc—acetic acid; BSA—bovine serum albumin; EDAC—ethyl dimethylaminopropyl carbodiimide; DDD—1,1 bis(p-chlorophenyl)—2,2 dichloroethane; BgG—Bovine gamma Globulin.

EXAMPLE I

Preparation of 1-p-nitrophenyl-2-succinamido-1,3-propanediol

Succinic anhydride (1.0 g, 10 mmol) in 30 ml THF was added dropwise over 3 h at room temperature into a heterogeneous solution of 2.12 g (1O mmol) of chloramphenicol base (Sigma) in 40 ml of methanol. The reaction mixture was allowed to stir at room temperature for 17 h. A solution of 0.5 g (5 mmol) of succinic anydride in 1O ml of THF was added dropwise and the reaction allowed to continue for 70 h at 4° C. to near completion. The reaction mixture was evaporated at room temperature, ethyl acetate was added and the organic layer was washed four times with 50 ml of water, twice with 50 ml of brine, dried with sodium sulfate and concentrated. Chromatographic separation on silica gel with methylene chloride-methanol-acetic acid (9/1/0.1:v/v/v) yielded 0.74 g (25%) of pure 1-p-nitrophenyl-2-succinamido-1, 3-propanediol, confirmed by NMR analysis.

EXAMPLE II

Preparation of 1-p-nitrophenyl-2-(succinamido-BSA)-1,3-propanediol

To a solution of 188 mg (0.60 mmol) of 1-p-nitrophenyl-2-succinamido-1,3-propanediol (Example I) at 0° C. under argon were added 81 mg (0.70 mmol) of NHS and 165 mg (0.80 mmol) of DCC. This solution was stirred at 4° C. for 18 h, filtered, evaporated, washed with hexane, reevaporated and dissolved in 10 ml of THF. This material was then added dropwise through a glass wool plugged pipet to a constantly stirred, cold solution of BSA (644 mg, 10 μmol) in phosphate/carbonate buffer (40 ml, pH8.1) and stirred at 4° C. for 42 h. The pH of the solution then was readjusted from 7.5 to 8.1 with solid sodium carbonate and stirred for an additional 22 h. The reaction mixture was centrifuged at 10,000 RPM at 4° C. for 30 minutes, chromatographed on Sephadex ® G-25 (100 g, 500 ml) and eluted with phosphate buffer (pH8.5). Dialysis of the protein solution five times in 4 l of water/ammonium hydroxide (pH10) for 24 h followed by lyophilization afforded 693 mg (83%) of the white protein conjugate. The hapten number was determined to be 24 by ultraviolet absorbance (UV) determination.

EXAMPLE III

Preparation of 1-p-nitrophenyl-2-(succinamido-BgG)-1,3-propanediol

To a solution of 10 mg (0.36 mmol) of 1-p-nitrophenyl-2-succinamido-1,3-propanediol (Example I) in 10 ml of THF at 0° C. under argon were added 83 mg (0.40 mmol) of DCC and 46 mg (0.46 mmol) of NHS. This mixture was allowed to stir for 6 h after which additional portions of DCC and NHS were added. Stirring for two additional hours gave one major spot on tlc indicating nearly complete formation of the NHS ester. The material was filtered, evaporated, washed with hexane, evaporated and redissolved in 10 ml of THF. This solution was then added through a glass wool plugged pipet to a cold, stirred solution of 900 mg (5.14 μmol) of BgG in 40 ml phosphate buffer (8.46 pH) and the reaction mixture was allowed to stir at 4° C. for 20 h. The pH was readjusted from 7.6 to 9.0 due to precipitation of the protein. After 25 h, of additional stirring, the reaction mixture was centrifuged at 10,000 RPM at 4° C. for 30 min, then dialized six times against 4 l of water/ammonium hydroxide (10 pH) for 23 h (a large degree of precipitation occurred in the dialysis bag). The material was lyophilized to afford 559 mg (51%) of white protein conjugate. The hapten number was found to be 25 by UV determination.

EXAMPLE IV

Preparation of 1-p-nitrophenyl-succinamido-1, 3-propanediol glucose-6-phosphate dehydrogenase conjugate Into a dry 2-necked flask were weighed 1-p-nitrophenyl-2-succinamido-1,3-propanediol (0.0039 g Example I), NHS (0.0018 g) and EDAC hydrochloride (0.0029 g). After further drying of the flask and its contents overnight, 250 μl dimethylformamide was added into the flask and the solution formed was stirred for 4 h at 25° C. 32 μl of this solution were slowly added over a period of 3.25 h to a 4° C. solution containing 0.0015 g glucose-6-phosphate dehydrogenase, 0.015 g glucose-6-phosphate disodium salt, 0.020 g of nicotinamide adenine dinucleotide (reduced form) in 0.5 ml of 0.055 M pH8 Tris buffer and 0.15 ml of carbitol. The pH of the reaction mixture throughout the 3.25 h period was maintained in a range from 8.5 to 9.5 using 0.1 N sodium hydroxide. At the end of the reaction period, the mixture was chromatographed on a 30.5×1.9 cm column of Sephadex® G-50 and eluted with 0.55 M Tris buffer containing 0.05% sodium azide and 0.005% trimerosal. Fractions (2.8 ml) were collected and those fractions containing high enzyme activity (usually fractions 6 to 9) were pooled and used as the succinyl-chloramphenicol glucose-6-phosphate dehydrogenase conjugate. Calculation of reactants used gave a hapten to enzyme ratio of 111.

The compositions of the subject invention provide for reagents which provide a sensitive accurate assay for chloramphenicol, distinguishing chloramphenicol from closely related metabolites which are encountered in patient samples. The anitgenic conjugate provides for the efficient production of antibodies having high affinity and high titer for chloramphenicol. The combination of the antibodies and enzyme conjugates result in an accurate rapid assay for chloramphenicol in serum.

Although the foregoing invention has been described in some detail by way of illustration and example for purposes of clarity of understanding, it will be obvious that certain changes and modifications may be practiced within the scope of the appended claims.

What is claimed is:
1. A compound of the formula:

wherein:
R is an aliphatic linking group of up to 12 atoms other than hydrogen having a chain of from 2 to 8 atoms consisting of carbon, nitrogen, and chalcogen of atomic no. 8 to 16;
Z is a poly(amino acid), consisting of polypeptides and proteins having 1 or more subunits, of at least 5000 molecular weight;
m is 0 or 1; and
n is a number between 1 and the molecular weight of Z divided by 500.

2. A compound according to claim 1, wherein R is a 1-oxopolymethylene of from 3 to 5 carbon atoms.

3. A compound according to claim 2, wherein R is of 3 carbon atoms.

4. A compound of the formula:

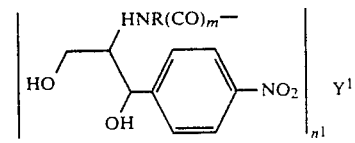

wherein:
R is a saturated aliphatic linking group of from 2 to 6 carbon atoms having from 0 to 1 oxo-carbonyl group at its terminus bonded to nitrogen;
$Y^1$ is a poly(amino acid); and
$n^1$ is a number between one and the molecular weight of $Y^1$ divided by 2000.

5. A compound according to claim 4, wherein R has an oxo-carbonyl at its terminus bonded to nitrogen and is of 3 carbon atoms.

6. A compound according to any of claims 4 or 5, wherein $Y^1$ is an antigen.

7. A compound according to any of claims 4 or 5, wherein $Y^1$ is an enzyme.

8. A compound according to claim 7, wherein said enzyme is flucose-6-phosphate dehydrogenase.

9. A compound of the formula:

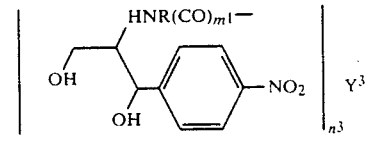

wherein:
$m^1$ is 0 or 1;
R is an aliphatic linking group of up to 12 atoms other than hydrogen having a chain of from 2 to 8 atoms consisting of carbon, nitrogen, and chalcogen of atomic no. 8 to 16;
$Y^3$ is an enzyme substituted at other than its active site its, having at least 30 percent of its activity prior to conjugation; and
$n^3$ is 1 to 30.

* * * * *